(12) United States Patent
Bolzoni

(10) Patent No.: US 6,387,872 B1
(45) Date of Patent: May 14, 2002

(54) DETERGENT COMPOSITION COMPRISING ALKOXYLATED AMINES

(75) Inventor: Giuseppe Vincenzo Bolzoni, Casalpusterlengo (IT)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 82 days.

(21) Appl. No.: 09/619,833

(22) Filed: Jul. 20, 2000

(30) Foreign Application Priority Data

Jul. 23, 1999 (EP) .............................................. 99202429
Jan. 7, 2000 (EP) .............................................. 00200049

(51) Int. Cl.$^7$ ................................................. C11D 3/30

(52) U.S. Cl. ........................ 510/499; 510/289; 510/356; 510/421

(58) Field of Search ................................ 510/289, 356, 510/421, 499

(56) References Cited

U.S. PATENT DOCUMENTS 5,409,574 A * 4/1995 Razac et al. ................. 162/156

* cited by examiner

Primary Examiner—Charles Boyer

(57) ABSTRACT

The invention concerns polyoxyethylene-polyoxypropylene aliphatic amines according to the general formula:

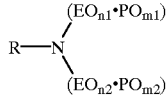

wherein R is a linear or branched saturated or unsaturated aliphatic group of 6–22 carbon atoms, n1 and n2 are each between 1 and 50 and represent the total number of EO groups in each chain and m1 and m2 are each between 1 and 10 and represent the total number of PO groups in each chain, with the proviso that the sums of n1 and n2 and of m1 and m2 are both at least 3, wherein in each chain the EO groups are present in discrete blocks of between 2 and 10 EO groups if that chain contains 2 or more EO groups and wherein in each chain the PO groups are present in discrete blocks of between 1 and 10 PO groups.

6 Claims, No Drawings

DETERGENT COMPOSITION COMPRISING ALKOXYLATED AMINES

FIELD OF THE INVENTION

The invention relates to alkoxylated amines and to detergent compositions containing such amines. More specifically the invention relates to ethoxylated propoxylated amines and their use in detergent compositions.

BACKGROUND TO THE INVENTION

Ethoxylated aliphatic amines are known in the art of detergents. Thus, EP-A-0 694 606 discloses hard surface cleaners comprising mixtures of ethoxylated/propoxylated fatty alcohols and ethoxylated fatty amines as foam suppressing agents. DE-A-44 12 380 (=WO 95/27768) discloses hard surface cleaners containing mixtures of ethoxylated fatty amines and fatty acids. EP-B-0 231 886 (=U.S. Pat. No. 5,145,608) discloses the use of ethoxylated fatty amines as solubilisers in concentrated cleaning compositions for bottle washing machines.

EP-B-0 112 593 discloses the use of ethoxylated amines as clay soil removal and antiredeposition agents in laundry detergents. It refers also to U.S. Pat. No. 4,171,278 which discloses cold water detergent compositions containing amines which are either ethoxylated or propoxylated.

WO 97/16514 discloses the use of polyethoxylated alkoxy-propylamines and polypropoxylated alkoxy-propylamines as foam enhancers and stabilisers, particularly in hand dishwash compositions.

EP-B-0 095 136 discloses machine dishwash rinse aids containing ethylene oxide adducts to propylene oxide/aliphatic (di)amine condensates which contain blocks of 5–50 mol ethylene oxide and blocks of 30–150 mol of propylene oxide. The exemplified products contain block condensates derived from ethylene diamine and from an unspecified aliphatic amine. Similar products are described in U.S. Pat. No. 4,062,814.

FR 2 459 830 discloses compositions for cleaning and descaling bathroom equipment comprising sulphamic acid and ethoxylated fatty amines as viscosity enhancers. GB 1 443 244 discloses similar compositions comprising ethoxylated or propoxylated fatty amines for the same purpose. Also, EP-B-0 276 501 discloses a large variety of tertiary amines together with aromatic sulfonate salt hydrotropes as viscosity enhancers in acid bathroom cleaners. Among the long list of amines mentioned are many ethoxylated and propoxylated fatty amines and a few symmetrical mixed ethoxylated/propoxylated fatty amines containing one ethyleneoxy and one propyleneoxy group in both alkoxy chains.

BRIEF DESCRIPTION OF THE INVENTION

Novel polyoxyethylene-polyoxypropylene aliphatic amines have now been found in which the ethyleneoxy and propyleneoxy groups are non-randomly distributed in the molecule. These alkoxylated amines have excellent surfactant properties and are therefore useful to be incorporated in a wide variety of detergent compositions. The alkoxylated amines may be prepared by alternatingly reacting an alkyl amine with ethylene oxide and with propylene oxide, each time until the reaction product contains the required average number of ethyleneoxy groups or propyleneoxy groups respectively.

DETAILED DESCRIPTION OF THE INVENTION

The polyoxyethylene-polyoxypropylene aliphatic amines according to the invention have the general formula below:

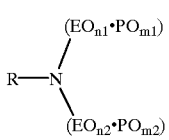

Formula 1 wherein R is a linear or branched saturated or unsaturated aliphatic group of 6–22 carbon atoms, n1 and n2 are each between 1 and 50 and represent the total number of EO groups in each chain and m1 and m2 are each between 1 and 10 and represent the total number of PO groups in each chain, with the proviso that the sums of n1 and n2 and of m1 and m2 are both at least 3, wherein in each chain the EO groups are present in discrete blocks of between 2 and 10 EO groups if that chain contains 2 or more EO groups and wherein in each chain the PO groups are present in discrete blocks of between 1 and 10 PO groups. EO stands for "ethyleneoxy" and PO stands for "1,2-propyleneoxy".

The polyoxyethylene-polyoxypropylene alkyl amines according to the invention may also be represented by the following general formula:

$$R-N-(EO_n \cdot PO_m)_2 \quad \text{Formula 2}$$

wherein R, EO and PO have the meaning given above and wherein n is the average of n1 and n2 and m is the average of m1 and m2 and n and m are at least 1.5. Generally, the difference between n1 and n2 is not more than three units and likewise m1 and m2 will not differ more than three units. Preferably the difference between n1 and n2 or between m1 and m2 will not be more than two units, more preferably at most one unit. Formula 2 is less precise in that in a particular molecule according to this formula both $EO_n PO_m$ chains need not necessarily be identical, but the formula nevertheless gives a good and concise representation of the compounds according to the invention.

Representative alkoxylated amines according to these general formulae may be represented by the following formulae:

$$R-N-(EO_a.PO_x)_2 \quad 2a$$
$$R-N-(EO_a.PO_x.EO_b.)_2 \quad 2b$$
$$R-N-(EO_a.PO_x.EO_b.PO_y)_2 \quad 2c$$
$$R-N-(EO_a.PO_x.EO_b.PO_y.EO_c)_2 \quad 2d$$
$$R-N-(EO_a.PO_x.EO_b.PO_y.EO_c.PO_z)_2, \text{ etc.} \quad 2e$$
$$R-N-(PO_x.EO_a)_2 \quad 2f$$
$$R-N-(PO_x.EO_a.PO_y)_2 \quad 2g$$
$$R-N-(PO_x.EO_a.PO_y.EO_b)_2 \quad 2h$$
$$R-N-(PO_x.EO_a.PO_y.EO_b.PO_z)_2 \quad 2i$$
$$R-N-(PO_x.EO_a.PO_y.EO_b.PO_z.EO_c)_2, \text{ etc.} \quad 2j$$

wherein each of a, b and c are between 1.5 and 10 and each of x, y and z are between 1 and 10 (preferably 1.5 and 10) and each represents the average number of EO groups and PO groups in each block of EO groups and each block of PO groups respectively, wherein a+b+c=n and x+y+z=m (wherein n and m refer to Formula 2). Preferably n is not higher than 30, more preferably not higher than 20

Preferably R has 8–22 carbon atoms. Suitable aliphatic amines have alkyl or alkenyl groups of 18 C-atoms or less, more preferably 16 or even 14 C-atoms or less, but preferably at least 9 or even 10. Suitable alkoxylated amines are those derived from fatty amines e.g. those with coconut, tallow, hardened tallow or oleyl fatty chains. Particularly suitable for environmental reasons are the alkoxylated amines having an aliphatic chain of 12 C-atoms or less.

The average numbers of propyleneoxy groups in each propyleneoxy block of the polyalkoxy chains, which in the formulae 2a–2j are represented by indices x, y and z, should preferably be between 1.5 and 4, more preferably 1.5–2.5, for alkoxylated amines with good biodegradability properties.

Preferred are the compounds in which the succession of ethylenoxy blocks and propyleneoxy blocks is as represented in the formulae 2a–2e, more preferably as represented in formula 2a. Preferably in formula 2a a is 2–10. Representative compounds according to this formula are those wherein a (the number of ethyleneoxy groups in each chain) is 3, 5 or 7 and x (the number of propyleneoxy groups in each chain) is 2.

The alkoxylated amines may be prepared using reaction conditions well known in the art for producing ethoxylated aliphatic amines and randomely mixed ethoxylated/propoxylated aliphatic amines using alkaline catalysts known for this purpose e.g. as described by M. D. Hoey and J. F. Gadberry in "Polyoxyethylene Alkylamines" and references cited therein.

The reaction is carried out by alternatingly reacting the aliphatic amine with ethylene oxide and with propylene oxide until in each ethyleneoxy block and propyleneoxy block the required number of ethyleneoxy groups and propyleneoxy groups respectively has been added. The aliphatic amine starting material may be derived from natural sources, i.e. vegetable or animal oils or fats, or they may be of synthetic origin, particularly if R is a branched aliphatic group.

Thus, as an example, $C_{18}H_{35}$—$N(EO_5PO_2)_2$ is prepared by first reacting oleyl amine with 10 molequivalent of ethylene oxide at 130–180° C. using potassium hydroxyde as the catalyst, followed by reacting the obtained addition product with 4 molequivalents of propylene oxide under the same reaction conditions.

To introduce further blocks of ethylenoxy groups and propyleneoxy groups, if desired, the obtained product is further reacted with the required amount of ethylene oxide to obtain the desired number of ethyleneoxy groups in each chain and thereafter with the required amount of propylene oxide to obtain the desired number of propylenoxy groups in each chain.

The synthesis methods described above generally give rise to mixtures of products with varying numbers of EO and PO groups in the polyalkoxy chains whereby the average values of these numbers in the mixture are determined by the mole ratio of amine (or alkoxylated amine)and ethylene oxide or propylene oxide used for each reaction step. Preferred are those mixtures in which the average number of EO groups per EO block in the polyalkoxy chains is at least 2, more preferably at least 2.5. Likewise preferred are those mixtures in which the average number of PO groups per PO block in the chains is 1.5–2.5, more preferably 1.8–2.3, most preferably 2.

The alkoxylated amines according to the invention are very efficient surfactants which have a very low critical micellar concentration. They may be combined with anionic, nonionic, cationic, amphoteric and zwitterionic surfactants known in the art.

They are excellently suitable for use in detergent compositions intended for application on laundry, all kinds of hard surfaces, soft furnishings, skin, hair, etc. The compounds generally have a high cloud point. Combination of the compounds of the invention with other surfactants, particularly anionic surfactants, leads to products with improved removal of fatty soil and enhanced solubility. Furthermore, they are very suitable for low foaming compositions and combinations of these alkoxylated amines with small amounts of fatty acid soap work effectively as antifoaming agents. Also, the compounds are easily and quickly soluble in any amount of water without any viscosity increase or gel formation. Finally, the compounds are useful as hydrotropes. These hydrotropic properties are particularly useful in concentrated detergent compositions which before or during use need to be diluted with water.

During dilution such detergent compositions often go through a concentration phase characterized by high viscosity and gel formation which makes further dilution difficult and time consuming. The addition of even a minor amount of the alkoxylated amines according to the invention drastically reduces peak viscosity and gel formation an provides easy dissolution to a homogeneous solution with any amount of water.

Detergent compositions for hard surface cleaning which contain the alkoxylated amines according to the invention show reduced streaking. Such compositions, which can also contain anionic polymers to obtain primary and secondary cleaning benefits, may be formulated with the alkoxylated amines at acidic as well as at neutral or mildly alkaline pH.

The alkoxylated amines behave like cationic surfactants at low pH, wheras under near neutral to alkaline conditions they behave increasingly like nonionic surfactants. They can be combined with a wide range of anionic, nonionic, cationic, amphoteric and zwitterionic surfactants.

Suitable anionic surfactants which may be combined with the amines according to the invention are water-soluble salts of organic sulphuric acid esters and sulphonic acids having in the molecular structure an alkyl group containing 8–22 C atoms or an alkylaryl group containing 6–20 C atoms in the alkyl part.

Examples of such anionic surfactants are water soluble salts of:

long chain (i.e. 8–22 C-atom) alcohol sulphates (hereinafter referred to as PAS), especially those obtained by sulphating the fatty alcohols produced by reducing the glycerides of tallow or coconut oil;

alkylbenzene-sulphonates, such as those in which the alkyl group contains from 6 to 20 carbon atoms;

secondary alkanesulphonates.

Also suitable are the salts of:

alkylglyceryl ether sulphates, especially of the ethers of fatty alcohols derived from tallow and coconut oil;

fatty acid monoglyceride sulphates;

sulphates of ethoxylated aliphatic alcohols containing 1–8 ethyleneoxy groups;

alkylphenol ethyleneoxy-ether sulphates with from 1 to 8 ethyleneoxy units per molecule and in which the alkyl groups contain from 4 to 14 carbon atoms;

the reaction product of fatty acids esterified with isethionic acid and neutralised with alkali.

Suitable nonionic surfactants can be broadly described as compounds produced by the condensation of simple alkylene oxides, which are hydrophilic in nature, with an organic hydrophobic compound which may be aliphatic or alkyl-aromatic in nature. The length of the hydrophilic or polyoxyalkylene chain which is attached to any particular hydrophobic group can be readily adjusted to yield a water-soluble compound having the desired balance between hydrophilic and hydrophobic elements. This enables the choice of nonionic surfactants with the right HLB.

Particular examples include the condensation products of aliphatic alcohols having from 8 to 22 carbon atoms in either straight or branched chain configuration with ethylene oxide, such as a coconut alcohol ethylene oxide condensates having from 2 to 15 moles of ethylene oxide per mole of coconut alcohol; condensates of alkylphenols having C6–C15 alkyl groups with 5 to 25 moles of ethylene oxide per mole of alkylphenol; condensates of the reaction product of ethylenediamine and propylene oxide with ethylene oxide, the condensates containing from 40 to 80% of ethyleneoxy groups by weight and having a molecular weight of from 5,000 to 11,000.

Other examples are: alkylglycosides, which are condensation products of long chain aliphatic alcohols and saccharides; tertiary amine oxides of structure RRRNO, where one R is an alkyl group of 8 to 20 carbon atoms and the other R's are each alkyl or hydroxyalkyl groups of 1 to 3 carbon atoms, e.g. dimethyldodecylamine oxide; tertiary phosphine oxides of structure RRRPO, where one R is an alkyl group of 8 to 20 carbon atoms and the other R's are each alkyl or hydroxyalkyl groups of 1 to 3 carbon atoms, for instance dimethyl-dodecylphosphine oxide; and dialkyl sulphoxides of structure RRSO where one R is an alkyl group of from 10 to 18 carbon atoms and the other is methyl or ethyl, for instance methyltetradecyl sulphoxide; fatty acid alkylolamides; alkylene oxide condensates of fatty acid alkylolamides; alkyl mercaptans. Ethoxylated aliphatic alcohols are particularly preferred.

Suitable amphoteric surfactants are derivatives of aliphatic secondary and tertiary amines containing an alkyl group of 8 to 20 carbon atoms and an aliphatic group substituted by an anionic water-solubilising group, for instance sodium 3-dodecylamino-propionate, sodium 3-dodecylaminopropane-sulphonate and sodium N-2-hydroxy-dodecyl-N-methyltaurate.

Suitable cationic surfactants are quaternary ammonium salts having one or two alkyl or aralkyl groups of from 8 to 20 carbon atoms and two or three small aliphatic (e.g. methyl) groups, for instance cetyltrimethyl ammonium bromide.

Suitable zwitterionic surfactants are derivatives of aliphatic quaternary ammonium, sulphonium and phosphonium compounds having an aliphatic group of from 8 to 18 carbon atoms and an aliphatic group substituted by an anionic water-solubilising group, for instance 3-(N,N-dimethyl-N-hexadecylammonium)-propane-1-sulphonate betaine, 3-(dodecyl methyl-sulphonium)-propane-1-sulphonate betaine and 3-(cetylmethyl-phosphonium)-ethanesulphonate betaine.

Further examples of suitable surfactants are compounds commonly used as surface-active agents given in the well-known textbooks "Surface Active Agents", Volume I by Schwartz and Perry and "Surface Active Agents and Detergents", Volume II by Schwartz, Perry and Berch.

The alkoxylated amines according to the invention can also be used in conjunction with other common components of detergent compositions such as: water-soluble and insoluble builders, chelating agents, hydrotropes, chlorine and peroxy bleaches, bleach activators, dyes, perfumes, organic and mineral acids and organic and mineral bases.

EXAMPLES

Example 1

$C_{18}H_{35}$—$N(EO_3.PO_2)_2$ (I), $C_{18}H_{35}$—$N(EO_5.PO_2)_2$ (II) and $C_{18}H_{35}$—$N(EO_7.PO_2)_2$ (III) were prepared starting from oleylamine according to methods known in the art and described above. The critical mycellar concentration (CMC) was measured at pH 4 and 25° C. using a Wilhelmy plate. The cloud points were determined of a 1% solution in water. The alkalinity number is expressed in mg KOH equiv./g. The specific gravity was determined in g/l at 50° C. All compounds were viscous liquids at 20° C. They could quickly and easily be converted into homogeneous aqueous solutions with any amount of water by brief stirring. The data specified above are tabulated below:

| Alkoxylated amine | I | II | III |
| --- | --- | --- | --- |
| CMC | 0.02 mM | — | — |
| Cloud point | 40° C. | 57° C. | 70° C. |
| Alkinity number | 72 | 60 | 50 |
| Specific gravity | 976 | 976 | 976 |

The viscosity of various mixtures of Compound I and an ethoxylated alcohol with water was measured and compared with that of mixtures only containing the ethoxylated alcohol:

| Ratio:Water/ surfactant | Viscosity of surfacant solution (in m.Pas at 21 sec-1) | |
| --- | --- | --- |
| | Ethoxylated alcohol only | Ethoxylated alcohol + Amine-EO/PO (ratio 80/20) |
| 25%–75% | 70 | 85 |
| 50%–50% | 1400 | 150 |
| 75%–25% | 45 | 25 |

Example 2

A general purpose hard surface cleaner, containing the compound I prepared according to Example 1, was prepared according to the following recipe (ingredients in % wt):

| LIAL 111-5EO (nonionic surfactant)* | 4.00 |
| --- | --- |
| Coco fatty acid | 0.30 |
| $C_{19}H_{35}$—N $(EO_3.PO_2)_2$ | 1.00 |
| Benzoisothiazolinone | 0.016 |
| Perfume | 0.40 |
| Demin water | up to 100. |

*Ethoxylated C11 alcohol nonionic surfactant marketed by Condea Chimica DAC.

Example 3

A laundry detergent powder, containing the compound I prepared according to Example 1, is prepared according to the following recipe (ingredients in % wt):

| LAS | 6.0 |
| --- | --- |
| Nonionic 7EO | 2.5 |
| Nonionic 3EO | 1.3 |
| PAS | 1.0 |
| LES | 2.0 |
| ODMHEAC Cationic | 1.0 |
| $C_{18}H_{35}$—N $(EO_3.PO_2)_2$ | 1.5 |

-continued

| | |
|---|---|
| Soap | 0.4 |
| Zeolite A24 | 22.1 |
| Soil release copolymer | 3.5 |
| Sodium carbonate | 23.0 |
| Sodium disilicate | 13.2 |
| TAED | 2.5 |
| Percarbonate | 16.0 |
| Protease | 0.4 |
| Lipase | 0.05 |
| Amylase | 0.1 |
| Cellulase | 0.2 |
| Fluorescer | 0.6 |
| Perfume | 1.0 |
| Water | up to 100 |

ODMHEAC: Oleyl Dimethyl Hydroxyethyl Ammonium Chloride

Example 4

A non-aqueous liquid laundry detergent, containing the compound I prepared according to Example 1, is prepared according to the following recipe (ingredients in % wt):

| | |
|---|---|
| LAS | 19.4 |
| Nonionic 5EO | 25.5 |
| LES | 0.5 |
| $C_{18}H_{35}$—N $(EO_3.PO_2)_2$ | 3.0 |
| Soap | 23.0 |
| Monoethanoiamine | 6.8 |
| Propylene glycol | 15.0 |
| Protease | 1.0 |
| Lipase | 0.2 |
| Water | 5.6 |

What is claimed is:

1. Detergent composition comprising a polyoxyethylene-polyoxypropylene aliphatic amine according to the general formula:

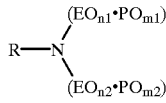

wherein R is a linear or branched saturated or unsaturated aliphatic group of 6–22 carbon atoms, n1 and n2 are each between 1 and 50 and represent the total number of EO groups in each chain and m1 and m2 are each between 1 and 10 and represent the total number of PO groups in each chain, with the proviso that n1 +n2 and m1 +m2 are both at least 3, wherein in each chain the EO groups are present in discrete blocks of between 2 and 10 EO groups if that chain contains 2 or more EO groups and wherein in each chain the PO groups are present in discrete blocks of between 1 and 10 PO groups and wherein EO stands for ethyleneoxy and PO stands for 1,2-propyleneoxy.

2. The detergent composition according to claim 1 wherein the difference between n1 and n2 is not more than 3 EO units and the difference between m1 and m2 is not more than 3 PO units.

3. The detergent composition according to claim 2 wherein the Polyoxyethylene-polyoxypropylene aliphatic amines are represented by any of the general formulae:

$$R-N-(EO_a.PO_x)_2$$

$$R-N-(EO_a.PO_x.EO_b.)_2$$

$$R-N-(EO_a.PO_x.EO_b.PO_y)_2$$

$$R-N-(EO_a.PO_x.EO_b.PO_y.EO_c)_2$$

$$R-N-(EO_a.PO_x.EO_b.PO_y.EO_c.PO_z)_2$$

$$R-N-(PO_x.EO_a.)_2$$

$$R-N-(PO_x.EO_a.PO_y)_2$$

$$R-N-(PO_x.EO_a.PO_y.EO_b)_2$$

$$R-N-(PO_x.EO_a.PO_y.EO_b.PO_z)_2$$

$$R-N-(PO_x.EO_a.PO_y.EO_b.PO_z.EO_c)_2$$

wherein each of a, b, c, x, y and z are between 1.5 and 10 and wherein a+b+c is between 1.5 and 30 and x+y+z is between 1.5 and 10.

4. The detergent composition according to claim 3 wherein x, y and z are between 1.5 and 4.

5. The detergent composition according to claim 3 wherein x, y and z are between 1.5 and 2.5.

6. The detergent composition according to claim 5 wherein the polyoxyethylene-polyoxypropylene aliphatic amines are represented by the formula:

$$R-N\ (EO_a.PO_x)_2$$

wherein a is between 2 and 10 and x is between 1.5 and 2.5.

* * * * *